(12) United States Patent
Mapoles et al.

(10) Patent No.: US 7,505,619 B2
(45) Date of Patent: Mar. 17, 2009

(54) SYSTEM AND METHOD FOR CONDUCTING ADAPTIVE FOURIER FILTERING TO DETECT DEFECTS IN DENSE LOGIC AREAS OF AN INSPECTION SURFACE

(75) Inventors: Evan R. Mapoles, San Ramon, CA (US); Grace H. Chen, San Jose, CA (US); Christopher F. Bevis, Los Gatos, CA (US); David W. Shortt, Milpitas, CA (US)

(73) Assignee: KLA-Tencor Technologies Corporation, Milpitas, CA (US)

( * ) Notice: Subject to any disclaimer, the term of this patent is extended or adjusted under 35 U.S.C. 154(b) by 417 days.

(21) Appl. No.: 11/314,779

(22) Filed: Dec. 20, 2005

(65) Prior Publication Data

US 2007/0081154 A1      Apr. 12, 2007

Related U.S. Application Data

(63) Continuation-in-part of application No. 10/315,713, filed on Dec. 9, 2002, now Pat. No. 7,106,432.

(60) Provisional application No. 60/414,206, filed on Sep. 27, 2002.

(51) Int. Cl.
*G06K 9/00*    (2006.01)

(52) U.S. Cl. ............. 382/149; 250/559.07; 250/559.41; 250/559.45; 348/126; 348/128; 356/237.3; 356/239.8; 356/600; 356/603; 382/144; 382/147

(58) Field of Classification Search ............ 250/559.07, 250/559.41, 559.45; 348/126, 128; 356/237.1, 356/237.2, 237.3, 237.4, 237.5, 239.1, 239.8, 356/432, 450, 502, 600, 602, 603, 604; 382/145, 382/147, 149, 144
See application file for complete search history.

(56) References Cited

U.S. PATENT DOCUMENTS 4,173,415 A    11/1979   Wyatt (Continued)

FOREIGN PATENT DOCUMENTS

JP    2001281097 A    10/2001

OTHER PUBLICATIONS

U.S. Appl. No. 10/315,713, filed Dec. 9, 2002, entitled: "Surface Inspection System and Method for Using Photo Detector Array to Detect Defects in Inspection Surface", by inventors Mapoles et al.

(Continued)

*Primary Examiner*—Gregory M Desire
(74) *Attorney, Agent, or Firm*—Suiter Swantz pc llo

(57) ABSTRACT

A dark field surface inspection tool and system are disclosed herein. The tool includes an illumination source capable of scanning a light beam onto an inspection surface. Light scattered by each inspection point is captured as image data by a photo detector array arranged at a fourier plane. The images captured are adaptively filtered to remove a portion of the bright pixels from the images to generate filtered images. The filtered images are then analyzed to detect defects in the inspection surface. Methods of the invention include using die-to-die comparison to identify bright portions of scattering patterns and generate unique image filters associated with those patterns. The associated images are then filtered to generate filtered images which are then used to detect defects. Also, data models of light scattering behavior can be used to generate filters.

30 Claims, 7 Drawing Sheets

U.S. PATENT DOCUMENTS

| | | | |
|---|---|---|---|
| 4,511,803 A | 4/1985 | Röss et al. | |
| 4,583,861 A | 4/1986 | Yamaji et al. | |
| 4,710,642 A | 12/1987 | McNeil | |
| 4,991,971 A | 2/1991 | Geary et al. | |
| 5,138,180 A * | 8/1992 | Yamanaka | 250/559.07 |
| 5,204,910 A | 4/1993 | Lebeau | |
| 5,293,538 A * | 3/1994 | Iwata et al. | 356/239.1 |
| 5,365,330 A * | 11/1994 | Hagiwara | 356/237.3 |
| 5,428,442 A * | 6/1995 | Lin et al. | 356/237.5 |
| 5,444,529 A * | 8/1995 | Tateiwa | 356/337 |
| 5,450,204 A * | 9/1995 | Shigeyama et al. | 356/604 |
| 5,621,811 A * | 4/1997 | Roder et al. | 382/147 |
| 5,717,485 A * | 2/1998 | Ito et al. | 356/237.1 |
| 5,790,251 A | 8/1998 | Hagiwara | |
| 5,798,831 A | 8/1998 | Hagiwara | |
| 5,805,278 A * | 9/1998 | Danko | 356/237.1 |
| 5,991,038 A * | 11/1999 | Yamamoto | 356/600 |
| 6,020,957 A * | 2/2000 | Rosengaus et al. | 356/237.4 |
| 6,034,776 A | 3/2000 | Germer et al. | |
| 6,078,386 A * | 6/2000 | Tsai et al. | 356/237.1 |
| 6,084,664 A * | 7/2000 | Matsumoto et al. | 356/237.4 |
| 6,178,257 B1 | 1/2001 | Alumot et al. | |
| 6,259,521 B1 | 7/2001 | Miller et al. | |
| 6,262,803 B1 * | 7/2001 | Hallerman et al. | 356/603 |
| 6,271,916 B1 | 8/2001 | Marxer et al. | |
| 6,333,785 B1 | 12/2001 | Schmolke et al. | |
| 6,411,377 B1 | 6/2002 | Noguchi et al. | |
| 6,496,270 B1 * | 12/2002 | Kelley et al. | 356/602 |
| 6,534,222 B1 | 3/2003 | Suzuki | |
| 6,562,248 B1 | 5/2003 | Subramanian et al. | |
| 6,603,541 B2 | 8/2003 | Lange | |
| 6,603,542 B1 * | 8/2003 | Chase et al. | 356/237.4 |
| 6,621,568 B1 | 9/2003 | Yonezawa | |
| 6,621,570 B1 * | 9/2003 | Danko | 356/237.4 |
| 6,630,996 B2 * | 10/2003 | Rao et al. | 356/237.5 |
| 6,643,004 B2 | 11/2003 | Detweiler et al. | |
| 6,643,007 B2 * | 11/2003 | Le | 356/237.3 |
| 6,661,912 B1 * | 12/2003 | Taguchi et al. | 382/145 |
| 6,836,336 B2 * | 12/2004 | Deason et al. | 356/502 |
| 7,002,677 B2 * | 2/2006 | Bevis et al. | 356/237.5 |
| 7,061,598 B1 * | 6/2006 | Bevis et al. | 356/237.1 |
| 7,106,432 B1 * | 9/2006 | Mapoles et al. | 356/237.2 |
| 2002/0088952 A1* | 7/2002 | Rao et al. | 250/559.45 |
| 2002/0126732 A1* | 9/2002 | Shakouri et al. | 374/130 |
| 2002/0145732 A1* | 10/2002 | Vaez-Iravani et al. | 356/237.2 |
| 2003/0218741 A1 | 11/2003 | Guetta | |
| 2004/0016896 A1 | 1/2004 | Almogy et al. | |
| 2004/0188643 A1* | 9/2004 | Weiss et al. | 250/559.42 |
| 2005/0018183 A1* | 1/2005 | Shortt | 356/239.1 |
| 2005/0122508 A1* | 6/2005 | Uto et al. | 356/237.2 |
| 2007/0081154 A1* | 4/2007 | Mapoles et al. | 356/237.5 |

OTHER PUBLICATIONS

Handbook of Optics, vol. 1, Fundamentals, Techniques, and Design, Second Edition, 1995, McGraw-Hill, Inc., pp. 30.4-30.8.
International Search Report in corresponding International Application No. PCT/US06/48089, mailed Jul. 8, 2008.
Written Opinion in corresponding International Application No. PCT/US06/48089, mailed Jul. 8, 2008.

* cited by examiner

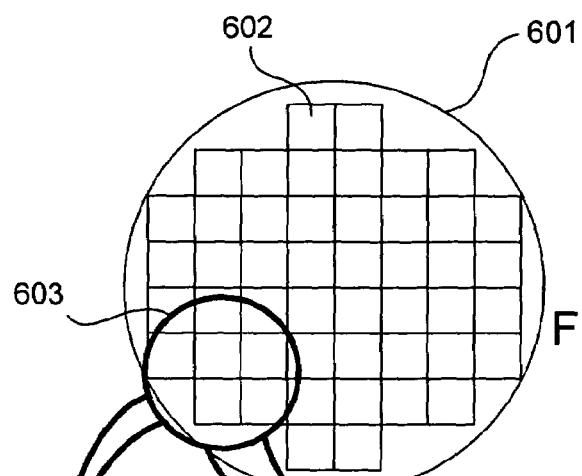
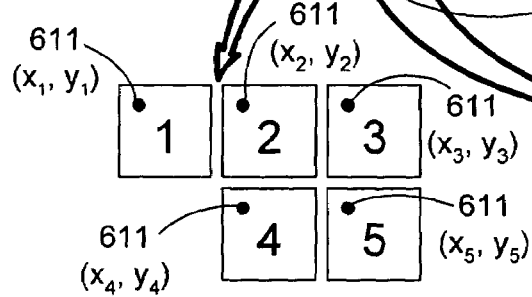
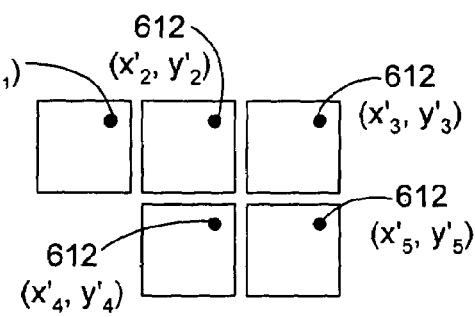
Fig. 6(a)
Fig. 6(b)
Fig. 6(c)

SYSTEM AND METHOD FOR CONDUCTING ADAPTIVE FOURIER FILTERING TO DETECT DEFECTS IN DENSE LOGIC AREAS OF AN INSPECTION SURFACE

RELATED APPLICATIONS

This application is a CIP to U. S. patent application entitled Surface Inspection System and Method For Using Photodetector Array to Detect Defects In Inspection Surface" filed on Dec. 9, 2002 having Ser. No 10/315,713 now U.S. Pat. No. 7,106,432 by inventors Evan R. Mapoles et al., and also claims priority to U.S. Provisional Patent Application Ser. No. 60/414,206, entitled "Darkfield Inspection System Having Photodetector Array", by inventors Christopher F. Bevis et al., filed on Sep. 27, 2002 the content of which are both incorporated by reference.

This application is related to the concurrently filed U.S. patent application entitled "Darkfield Inspection System Having Photodetector Array", by inventors Christopher F. Bevis et al., which is hereby incorporated by reference.

TECHNICAL FIELD

The invention described herein relates generally to surface inspection and testing. In particular, the invention relates to devices and methods for adaptively filtering signals used to detect defects in dense logic areas of an inspection surface.

BACKGROUND OF THE INVENTION

For many years, dark field scanning methodologies have been used to scan surfaces. Dark field scanning makes use of light scattered by the surface features to characterize and examine features of the surface. Such darkfield scanning can be used to detect defects in an inspected surface. In particular, semiconductor wafer surfaces and associated masks are subject to such scanning and inspection. In common usage, defects are frequently detected as aberrant light scattering features.

As is known to those having ordinary skill in the art, defects are fairly uncommon in the inspected surfaces. However, the consequences of such defects can be quite serious. The fact that defects occur in only one of many die patterns on a wafer or mask can be advantageously exploited by process engineers to detect defects. Consequently, defect detection is aided by systems that can compare the scattering patterns from multiple dies on a wafer and identify features which occur only in an isolated die. Such methodologies are commonly called die-to-die comparisons. Such defects can include, but are not limited to, pits, bumps, scratches, particles, process irregularities, and a number of other features which mar the surface. The presence of such defects on an inspection surface frequently cause a variation from the ordinary expected scattering pattern.

In dark field inspection a surface is illuminated by a light source and a single discrete light detector (placed so that it is not in the path of the reflected beam) is used to detect the light scattered by the surface. Thus, the background (the field) is dark. The scattered light received by the detector provides a representation of the surface where surface defects show up as lighter regions against the dark background or field. Hence, the name dark field scanning.

One of the problems in such dark field scanning is that for some surfaces the ordinary scattering pattern includes substantial regions of very bright signal. This bright signal can make the process of defect detection much more difficult as defects also produce bright signals. Thus, it is important to be able to differentiate defect caused signal from the ordinary scattering pattern.

In a conventional dark field surface inspection device an incident light beam is directed onto an inspection surface to generate a scattering pattern. The scattered light is collected by a lens or reflector and focused onto one or more discrete photodetector elements (for example PMT (photomultiplier tubes)). Alternative technologies direct the light onto a photodetector arranged in a spatial plane. By integrating light information from the photodetector elements, the presence of a defect can be determined.

A problem with such prior art systems is that they have difficulty discerning defect scatter from ordinary scatter generated by a patterned surface. Frequently, when patterned surfaces (e.g., the patterned surfaces of semiconductor wafers) are scanned, the resulting scattering pattern is detected as a "defect" by the discrete photodetector element. Even in systems which employ die-to-die comparison, small variations in the surface pattern and the resulting variation in scattering can mislead the system into falsely identifying a defect. Thus, portions of the (otherwise defect-free) patterned surface give false readings, as if they had defects in the surface. Conventional devices have attempted to circumvent this problem by so-called Fourier filtering. Under plane wave illumination, the intensity distribution at the back focal plane of a lens is proportional to the Fourier transform of the object. Further, for a repeating surface pattern (such as, for example a semiconductor memory array), the Fourier transform consists of a pattern of light and dark areas which remain constant as the wafer is scanned. By placing a filter in the back focal plane of the lens, the brightest portions of the signal can be blocked (filtered). In other words, filter having a selected pattern of opaque regions can be used to selectively and physically block the brightest portions of the optical signal generated by the repeating surface pattern. Thus, artifacts of repeating surface pattern can be filtered out and leave only non-repeating signals from particles and other defects. Such Fourier filtering is a common technology employed in wafer inspection machines from many manufacturers.

One of the limitations of Fourier filtering based instruments is that they can only inspect areas with repeating patterns (for example, arrays of memory cells) or blank areas. Critically, Fourier filtering of the type previously described is not useful for inspecting non-uniform surfaces like random logic areas. This poses a significant fundamental limitation on the technology.

For example, in a prior art machine such as the Hitachi Model IS-2300 inspection machine, darkfield Fourier filtering is combined with die-to-die image subtraction to effectuate wafer inspection. Using this technique, non-repeating pattern areas on a wafer can be inspected by the die-to-die comparison. However, even with such die-to-die comparison, conventional technologies still need Fourier filtering to obtain good sensitivity in the repeating array areas. For example, in dense memory cell areas of a wafer, a darkfield signal from the circuit pattern is usually so much stronger than that from the circuit lines in the peripheral areas that the dynamic range of the sensors are exceeded. As a result, either small particles in the array areas cannot be seen due to saturation, or small particles in the peripheral areas cannot be detected due to insufficient signal strength. Fourier filtering equalizes the darkfield signal so that small particles can be detected in dense or sparse areas at the same time.

Although prior art techniques are relatively capable of detecting particle type defects, their sensitivity to pattern defects is very poor. Additionally, since filtered images are usually dark without circuit features, it is not possible to do an accurate die-to-die image alignment, which is necessary for achieving good cancellation in a subtraction algorithm. One solution is to use an expensive mechanical stage of very high precision, but even with such a stage, due to the pattern placement variations on the wafer and residual errors of the stage, the achievable sensitivity is limited roughly to particles that are 0.5 μm and larger. This limit comes from the alignment errors in die-to-die image subtraction. Additionally, the filtering makes it difficult to detect defects in certain regions of the surface. Moreover, as surface patterns become more complicated (as is the case in modern VLSI circuit structures), the patterns become more complex, and more filtering must be implemented. As a result, less and less of the surface can be effectively scanned for defects. Additionally, although Fourier filtering can be extremely effective in filtering light scattered by regularly repeating array areas (e.g., memory cells), there is currently no similar technique that can be applied to areas of the wafer where the surface pattern is not regular and repeating. Examples of such areas include random logic areas. Unlike memory areas (which feature repeating surface patterns), areas without repeating surface patterns are far more difficult to filter. This is because the scattering pattern at the Fourier transform plane of a lens is not constant as the wafer is scanned. As a result, it is no longer practical to insert a fixed filter to selectively block light scattering caused by the surface pattern. Heretofore, there has not been a tool or methodology of providing fourier filtering of data obtained in dense logic areas or other surface areas having non-repeating surface patterns.

What is needed are dark field inspection tools and methodologies that can achieve filtering of the scattering signal in the presence of non-repeating surface patterns. Adaptively filtering the signal to accommodate surface features such as dense logic areas would be highly advantageous.

BRIEF SUMMARY OF THE INVENTION

In accordance with the principles of the present invention, tools and methods for adaptive fourier filtering of light signals in a using dark field inspection tool are disclosed.

In general, the invention includes a system and method for conducting adaptive fourier filtering to detect defects of an inspection surface. In certain particular embodiments, the invention includes tools and methods enabling the inspection of a portion of a surface having non-repeating surface patterns such as dense logic areas of a surface. In particular, certain embodiments of the invention adaptively filter out the brightest pixels of an image to produce a filtered image that can have enhanced defect detection properties. The filters can be obtained using a number of different approaches including, but not limited to die-to-die comparison and filtering based on data models. One particularly advantageous feature of the invention is the ability to conduct such filtering even on portions of the inspection surface that have non-repeating surface patterns. Additionally, since all the original image data is maintained, several different analyses can be performed on the same inspection surface without the need for new testing for each analysis.

One embodiment of the invention includes a dark field surface inspection system with an illumination source for directing a light beam onto a work piece to generate light scattering patterns from selected portions of the inspection surface. The system also includes a photodetector array arranged at a fourier plane to receive images of the light scattering patterns. Typically, the array comprises a two-dimensional array of light sensitive pixels. Circuitry for receiving the images and conducting adaptive fourier filtering of image data is part of the system. The circuitry employs adaptive filtering of image to selectively filter image pixels to generate filtered images. Additionally, the circuitry enables storage of the original image data before filtering. The filtered images can, for example, enhance signal to noise ratio in the filtered images.

The invention also includes surface inspection methods. In one method embodiment, selected portions of an inspection surface are illuminated with a light beam to generate a light scattering pattern associated with the selected portions of the inspection surface. The resulting image data is captured at a fourier plane. Said images are captured as two-dimensional images. The image data is then adaptively filtered to produce filtered images that have selected image pixels removed from the image. Optionally, these filtered images are analyzed for the presence of defects in the associated portions of the inspection surface.

Embodiments of the invention can generate adaptive filters using a die-to-die comparison of inspection surface. Also, data models of the inspection surface can be used to identify selected bright portions of images and selectively filter these portions out of the filtered images. Also, other filtering approaches can be used in accordance with the principles of the invention.

These and other aspects of the present invention are described in greater detail in the detailed description of the drawings set forth hereinbelow.

BRIEF DESCRIPTION OF THE DRAWINGS

The following detailed description will be more readily understood in conjunction with the accompanying drawings, in which:

FIG. 6(a) is a simplified schematic plan view of a semiconductor wafer with a plurality of semiconductor dies formed thereon.

FIG. 6(b) is a simplified and expanded schematic view of a portion of the wafer depicted in FIG. 6(a) showing the same inspection point on a plurality of different dies.

FIG. 6(c) is another is a simplified and expanded schematic of a portion of the wafer depicted in FIG. 6(a) showing another inspection point on a plurality of different dies.

It is to be understood that, in the drawings, like reference numerals designate like structural elements. Also, it is understood that the depictions in the Figures are not necessarily to scale.

DETAILED DESCRIPTION OF EMBODIMENTS OF THE INVENTION

The present invention has been particularly shown and described with respect to certain embodiments and specific features thereof. The embodiments set forth herein below are to be taken as illustrative rather than limiting. It should be readily apparent to those of ordinary skill in the art that various changes and modifications in form and detail may be made without departing from the spirit and scope of the invention.

In general, adaptive filtering in accordance with the principles of the invention works as follows. A light beam is directed onto a target and scattered into a scattering pattern. The scattering pattern is collected by a photodetector array in a fourier plane to form an image of the pattern. The brightest pixels of the pattern are adaptively filtered out. And the remaining pixels are processed to detect defects. Because these brightest pixels change for each point on the inspection surface, there is a need for a highly adaptive filtering system that is constantly adjusted with the changing nature of the exact point on the inspection surface.

Figure 1:
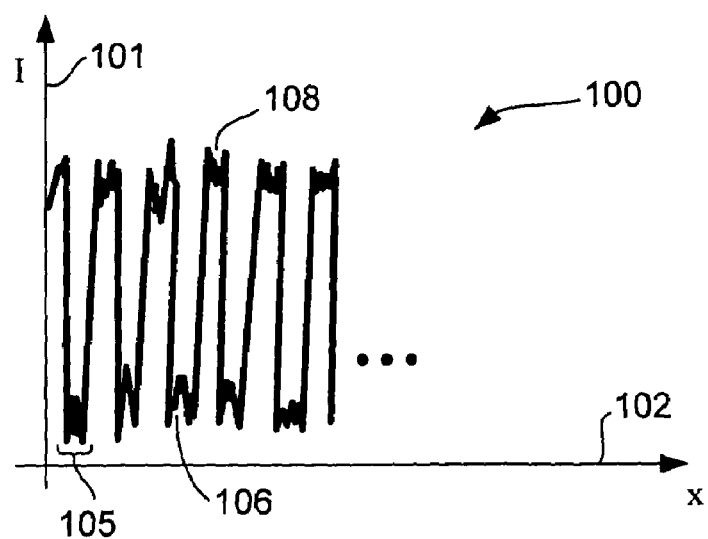
FIG. 1 is simplified graphical depiction of a plot of light intensity as a function of spatial coordinate generated by a repeating pattern formed on an inspection surface.
Figure 2:
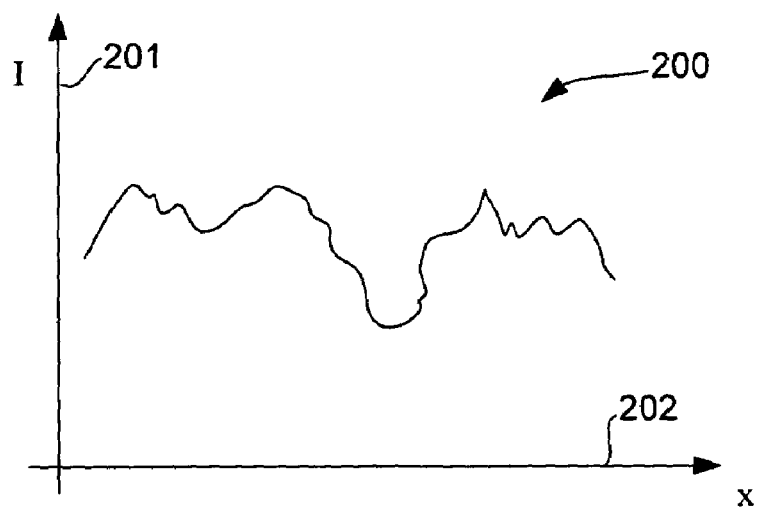
FIG. 2 is simplified graphical depiction of a plot of light intensity as a function of spatial coordinate generated by a non-repeating pattern formed on an inspection surface.

FIGS. 1 and 2 are used to provide a simplified explanation of some of the basic principles of the invention. The inspection surface can comprise many different surfaces, including, but not limited to semiconductor substrates having a plurality IC die patterns formed thereon or mask reticles having a mask pattern formed thereon. Additionally, the inspection surface can have many different surface conformations. For example, memory cells commonly feature a regular pattern of repeating surface patterns. In contrast, other portions of a surface may have a more or less random surface pattern. Such non-repeating patterns are frequently found in the logic areas of a die pattern or other associated surface areas.

As is known light is reflected, diffracted, and scattered from its surface at varying degrees of intensity. As a light beam is scanned over a die and light scattered from the surface is detected, a light intensity pattern emerges. FIG. 1 depicts a very simplified two-axis graph 100 of a light intensity pattern 105 (also referred to as a scattering pattern) produced by a regularly repeating surface pattern. The depicted graph presents the intensity profile in the spatial domain. This pattern relates to light scattered by a regular surface pattern such as a memory cell or other regular array pattern. The graph 100 plots light intensity 101 as a function of the location 102 on a die. Generally the light represents the light scattered from a repeating pattern of surface features. As can readily be seen, the scattering pattern is characterized by a somewhat predictable pattern high light intensity (light regions) 108 and low light intensity (dark regions) 106. Dark regions can be defined those regions where the light intensity falls below some intensity threshold. If each die inspected were perfectly identical, each light intensity pattern 105 would also be identical. In practice, the light intensity patterns are commonly very similar for regular array areas. The presence of defects can cause a light intensity pattern to vary. However, over many portions of the light scattering pattern, such variations in light intensity are difficult to detect. In particular, variations in light intensity are difficult to detect in the lighter regions 108 of the detected scattering pattern 105. However, because the dark regions 106 are black (or very nearly black), small variations in these regions can be detected by the increased amounts of light. These increased amounts of light are relatively easy to detect and can be used to identify defect candidates. This detectability in the dark regions is much enhanced by the back plane filtering discussed above. As a result of such filtering the signal-to-noise ration (S/N ratio) is significantly enhanced making the detection of defects easier. As can be seen from a quick viewing of FIG. 1, the regular pattern of light and dark regions cause lend themselves to an easy (comparatively speaking) filtering regime, analysis, and defect detection.

This is to be contrasted with the scattering pattern when a portion of a surface having non-repeating surface patterns is illuminated. FIG. 2 schematically depicts this situation. In FIG. 2, intensity 201 is plotted as a function of spatial position 202 in graph 200. It is clear in FIG. 2 that no regular pattern of dark and light regions is easily discernable. This has been one of the problems plaguing the inspection industry for some time. This problem presents one of the great difficulties involved in inspecting dense random logic areas of a surface. This problem and the inventors solution will be explained in greater detail in the following paragraphs where scattering patterns are analyzed in the fourier transform plane.

One of the aspects of the present invention is to extend the prior art concept of filtering beyond the very limited realm of regular surface patterns. The idea being to the advantages of some type of filtering beyond its narrow application to regular memory array type surface structures. The idea being that with care a similar concept might be discovered that can be applied to non-regular surfaces.

Figure 3:
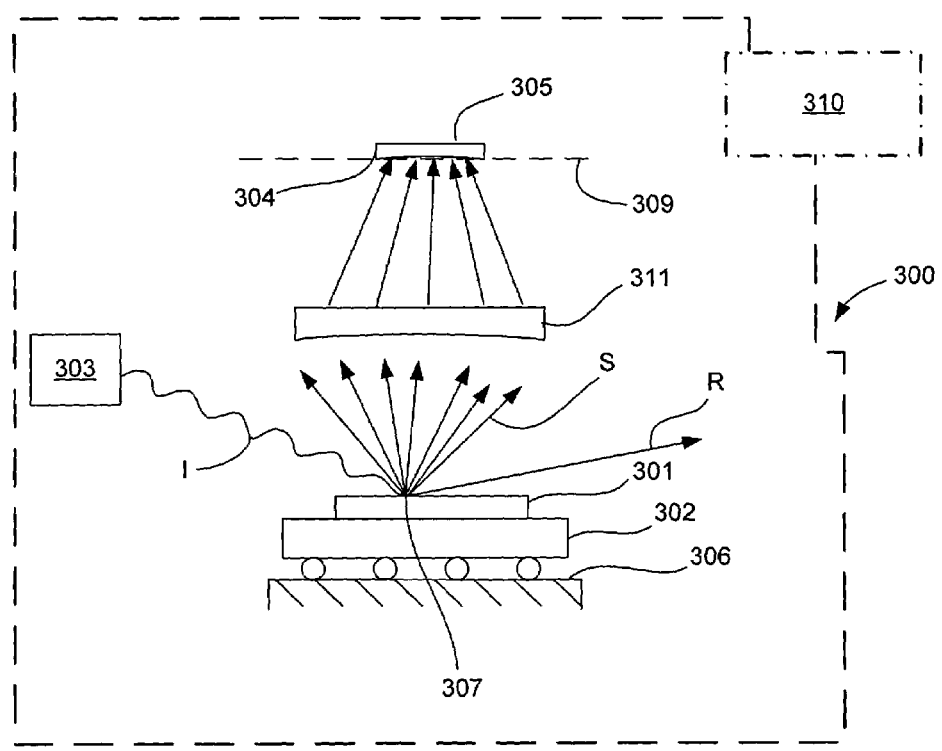
FIG. 3 is simplified schematic depiction of an example system embodiment constructed to detect defects in an inspection surface in accordance with the principles of the invention.

FIG. 3 depicts a system 300 embodiment constructed in accordance with the principles of the invention configured to inspect an inspection surface (also, referred to interchangeably as the target, work piece, or substrate) 301. As used herein, substrate 301 refers to any inspected surface. Typical examples include, but are not limited to, semiconductor wafers, pattern mask reticles, or other like substrates. The embodiments of the invention have particular utility when used on patterned semiconductor wafers 301 that have several semiconductor dies formed thereon. In particular, the invention finds enhanced utility when applied to surfaces that have die patterns with portions featuring non-recurring surface conformation patterns formed thereon. In use, the substrate 301 is typically positioned on a support 302, such as an electrostatic chuck or other commonly used apparatuses used for such purposes. An illumination source 303 directs a light beam I onto the target 301 to form a light spot on the surface. The spot generates a reflected beam R and creates scattered light beams S, which are received by photosensitive elements 304 of a photo detector array 305.

A scanning element 306 moves the inspection surface 301 and light beam I relative to one another so that the beam I scans a desired path over the surface of the inspection surface 301. Commonly, the scanning element includes a movable stage constructed for extremely precise movement so that a small beam of light can be scanned across the inspection surface. Thus, during inspection, the light beam I illuminates specific portions of the surface (also referred to herein as inspection points 307) on the inspection surface 301 to generate the light scattering pattern. The photo detector array 305 is arranged at a fourier plane to capture images of light scattering patterns generated as the beam I scans a desired path over the substrate 301. Although not required, systems typically include a beam-shaping element 311 configured to optically shape the beam to enhance the fourier distribution of the scattered light. Commonly, a fourier lens is used. However, other optical systems capable of similarly shaping the collected scattered light can be employed. Examples may include but are not limited to holographic optical elements, diffractive optical, reflective optics, lenses and combination optical elements. The photodetector array 305 is electrically connected to signal processing circuitry 310, which can receive image data from the photo detector array 305. The circuitry 310 can perform a number of electronic processes on the image data. Typically, such processes include, but are not limited to, image storage, image filtering, data analysis, image comparison, as well as other image processes known to those having ordinary skill in the art. Of particular importance to the present invention is the fact that the circuitry 310 can perform adaptive fourier filtering of data collected with the system. It should be especially noted that the data used for filtering and other image processing can be off-loaded to another microprocessor for processing.

The illumination source 303 depicted in FIG. 3 is typically a laser, although other sources can be used. In one implementation, the laser is an argon (Ar) ion laser. Such lasers typically emit light beams having wavelengths ($\lambda$) of 365 nm (nanometers), 488 nm, 532 nm, as well as other wavelengths. Such laser light beams produce a light dot having a spot size on the surface of the target. The light dots can be circular or ellipsoidal. As is also known to persons having ordinary skill in the art each illumination source 303 is characterized by an illumination solid angle. As is also known to persons having ordinary skill in the art, the illumination solid angle is related to the spot size of the system. Spot sizes typically range from about 10 microns ($\mu$) down into the sub-micron range. One common implementation is an elliptical light dot having a spot size of about 3 $\mu$ along the minor axis and about 10 $\mu$ along the major axis. Another common implementation is a circular light dot having a spot size of about 3 $\mu$ in diameter. Light dots are scanned across the surface of the work piece in a desired pattern enabling the desired portions of the surface to be inspected.

Such scanning is accomplished using a scanning element 306 that can comprise a wide variety of scanning devices known to persons having ordinary skill in the art. Suitable scanning elements 306 include, but are not limited to, devices that scan the beam I across the target 301 by moving the target 301 relative to the light beam I. In other implementations, the scanning element moves the light beam I relative to the target 301 thereby scanning the beam I across the surface of the target 301. In some other implementations, the beam I can be moved by moving the illumination source 303 relative to the target 301. In another alternative embodiment, the beam I is directed onto a moving mirror, or array of mirrors that are configured to direct the beam I onto the target 301 in a desired inspection pattern. As is known to those having ordinary skill in the art, many other implementations of scanning elements can be used in accordance with the principles of the present invention.

Still referring to FIG. 3, a photo detector array 305 is arranged along a detection surface 309. Suitable detection surfaces 309 include Fourier planes. In the depicted embodiment, the photo detector array 305 is arranged in a planar configuration. Curved configurations can also be used. As is known to those having ordinary skill in the art, other arrangements are possible. In the depicted preferred embodiment, the photosensitive elements 304 of the photo detector array 305 are each sized so that they are about the same size as or smaller than the illumination solid angle for the source 303. Additionally, there should be enough photosensitive elements in the detector so that the images include enough "dark" pixels (commonly about five or more). Preferably, such arrays include 100 or more photosensitive elements (e.g., 10×10 photo arrays). However, in theory, an array of 2×2 pixels is sufficient under the right conditions. However, common implementations employ arrays having 256 pixels (i.e., photosensitive elements). Of course the minimum solid angle subtended by a photo detector array 305 is determined by the size and number of photosensitive elements comprising the photo detector array 305. Factors like the spot size, wavelength of illuminating light, the illumination solid angle, fabrication constraints on minimum pixel size, as well as other factors play a role in the solid angle subtended by the photo detector array 305. In one example implementation, the photosensitive elements 304 of the photo detector array 305 are arranged so that they subtend a solid angle of greater than about 40° (angular degrees) by 40°. The inventors also contemplate tools arranged to image full 180° solid angles.

Thus, in one embodiment a photo detector array 305 is configured such that the photosensitive elements of a photo detector array are arranged about an inspection point 307 to cover a solid angle of greater than about 40° by 40°. The photo detector array 305 can be arranged having solid angles of less than 40° by 40°, but such arrangements are generally less effective at adaptive Fourier filtering because fewer dark regions are captured by the photo detector array 305.

The photo detector array 305 is preferable formed using an array type photodetector with a plurality of photosensitive elements 304. Commonly, these photosensitive elements comprise charge-coupled devices (CCD's), CMOS detectors, TDI detector and the like. However, the photo detector array 305 can be formed of a number of light sensitive detector devices including, without limitation, photodiodes, photo multiplier tubes (PMT's), charge-coupled array devices (CCD arrays), CMOS detectors, TDI detector arrays, and a variety of other light sensing devices known to those having ordinary skill in the art. As previously discussed, the photosensitive elements are sized so that they subtend solid angles on the order of the illumination solid angle for the illumination source. As is known to persons having ordinary skill in the art such illumination solid angle is related to spot size. In preferred embodiments, each of the photosensitive elements has a size that is related to the $\lambda$ of the incident light beam and the spot size for the light beam. In one implementation, each of the photosensitive elements is configured such that it subtends an angle defined by the $\lambda$ of the incident light beam divided by the spot size for the light beam ($\lambda$/spot size). For example, using a laser having a $\lambda$ of 532 nm, and a spot size of 3$\mu$ in diameter, the angle is defined as 0.532/3 radians or about 10.2°. Thus subtending a solid angle of about 10.2° by 10.2°. However, as with all such optical systems, there is a trade off between sensitivity (lots of samples) and speed. Thus, in preferred implementations using a 3$\mu$ spot size, suitable solid angles can range from about 1.75° to 4°. However, a wider range of sizes for photosensitive elements can be employed such that they subtend angles in the range of about 1.5° to about 12°. As can be appreciated by those with ordinary skill in the art, the actual size of the photosensitive elements 704 is determined by a number of factors, including, but not limited to $\lambda$ of the light, spot size, illumination solid angle, and distance the photosensitive elements are away from the inspection surface.

With continuing reference to FIG. 3, light from the beam I is directed onto the work piece 301 where it scatters as a plurality of scattered light beams S forming a light scattering pattern associated with the surface characteristics of the work piece 301. These beams S are detected and captured as images by the photo detector array 305. The photo detector array 305 can be used to capture images of the scattering pattern for each illuminated inspection point 307 on the work piece 301. These images comprise patterns of light and dark regions that can be compared with each other or with a reference image to locate defects. Reference images can be generated from die-to-die comparison or by using a digital model of the optical light scattering performance generated from a database model of the workpiece. These reference images are employed to generate a filter template used in embodiments of the invention.

As previously explained, the prior art applying opaque filters to enhance S/N ratio for inspecting regular array surface structures. The invention is intended to go beyond this basic technology. Embodiments of the invention are intended to scan for defects in the heretofore difficult to inspect random logic areas on an inspection surface.

Figure 4:
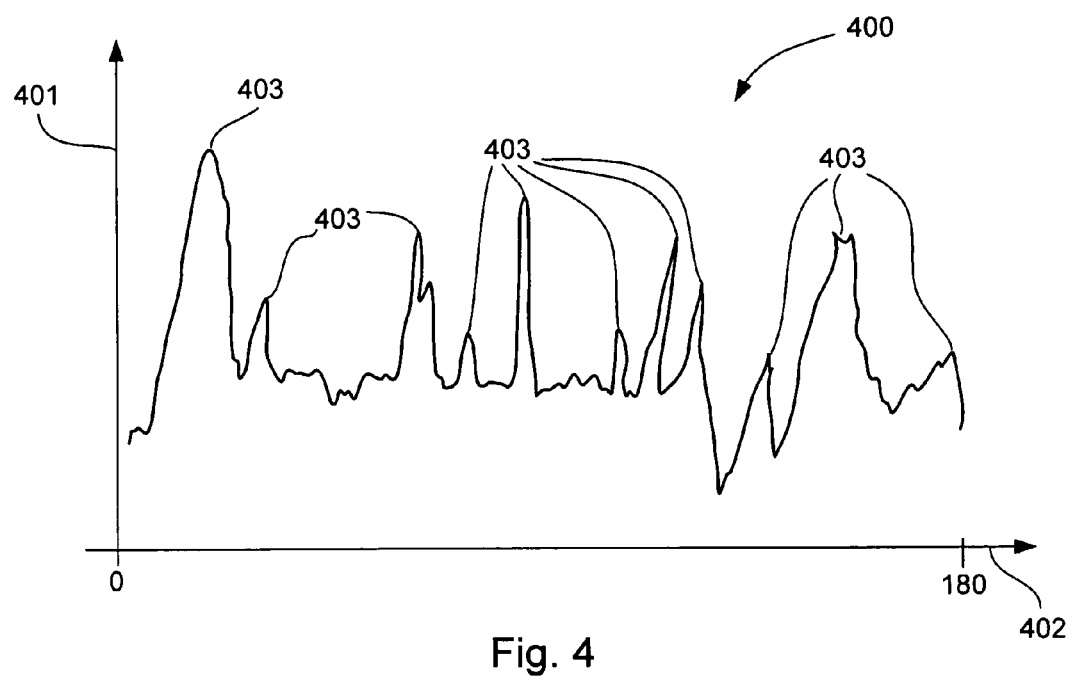
FIG. 4 is simplified graphical depiction of a plot of light intensity as a function of angular coordinate taken at a fourier plane and generated by a non-repeating pattern formed on an inspection surface.

FIG. 4 is a simplified schematic depiction of a 2-D (two dimensional) light distribution in the fourier plane for a scattering pattern generated by a bean directed onto a non-regular surface pattern (for example, a random logic pattern). It is important to note that the light scattered from the surface is gathered in an optical system and then analyzed in the fourier plane (not the spatial plane or the back plane as done in the prior art). The graph 400 of FIG. 4 shows light intensity 401 plotted as a function of angular distribution (between 0 and 180 degrees) 402. A series of non-regular peaks can easily be discerned. There is no regular intensity pattern of relatively uniform width and spacing as is known in the prior art. Additionally, as the illuminated dot scans across the random logic array of the inspection surface a completely different scattering pattern is be imaged for each sequential inspection point. This is unlike the regular repeating pattern experienced when a surface of repeating patterns is scanned. Thus, the insertion of a standardized opaque filter at the back plane is not workable. A different filter would have to be constructed for every last piece of the surface. Millions of filters or more would be needed. Moreover, for each change in substrate new filter sets would be required. This is expensive and time consuming and not a realistic choice.

However, the inventors have constructed a system and method of adaptively filtering that can be applied to any surface without the need for sets of opaque filters.

In one implementation of the invention, a die-to-die analysis of an inspection surface is conducted. This means that each die is scanned with the illumination beam. For each scanned portion of the die, a two-dimensional image of the scattering pattern is captured at a fourier plane. All image data is captured and retained. Each image will have a two dimensional pattern of light and dark regions. Moreover, each image of a point on a die is associated with an analogous image of the same point on each of the other dies on the inspected wafer. These analogous images comprise a set of images that can be processed to generate a filter template associated with the portion of the die related to the set of images.

Each set of images is processed to define a set of "bright" pixels that will be used in the filter template. Such "bright" pixels can be pixels having an intensity above a set threshold. The "bright" pixels can be the brightest portion of pixels in the image. For example, the most intense 25% of pixels comprise the bright pixels. This percentage can be readily defined by the process engineer to optimize the results obtained by the filter. Additionally, the brightest intensity peaks can be defined as the bright pixels. For example, the brightest 10 peaks can comprise the bright pixels. Importantly, each set of images for a give point are processed together. Thus, outliers and aberrant readings can be processed out of the set of images. Averaging or other statistical data processing can be used to process the data. These concepts are all variations on a theme. Many methods of determining which pixels are "bright" are known to those having ordinary skill in the art.

Once a set of bright pixels is defined, these pixels are applied to form a filter template. This template is basically a 2-D map of the bright pixels in a set of images. These bright pixels are the filter pixels.

Each image in the set of images is then processed using the filter template to determine if the associated portion of the inspection surface contains defects. Such processing means that filter operates on the image data of each image to remove the filter pixels from the processed image to form a filtered image. Thus, the bright pixels, as defined by filter template, are not used in any filtered images. The filtering, in effect, turns the pixels off. The filtered images are then evaluated for defects using any standard process known in the art. It is important to point out that all data from each image is retained and it is only during processing that the selected data is "filtered out". This means that the filter templates can be altered and the same data analyzed again if desired.

One major advantage of such technique is process is that the images for each individual portion of the inspection surface can be individually filtered with a unique filter template optimized for that portion of the surface. Additionally, because all the image data is retained, the filter template can be changed to analyze the data in many different manners before a final result is obtained. This is very different from the prior art where the physical nature of the template removes any flexibility from the analysis. Also, the present invention adapts the filter for each portion of the inspection surface creating unique individualized filters for each inspection point on the die.

Additionally, a data model of a given portion of the inspection surface can be used to generate a simulated image for that portion of the surface which can then be used for such adaptive filtering. For example, information concerning the surface can be compiled into a database and then predictive light scattering models can be run on the data thereby generating a predicted light scattering pattern for each portion of the surface. Then ordinary analysis can be performed on the images generated by the model to identify and otherwise characterize the brightness peaks and identify the "bright" pixels for the images. Then filter templates can be created as above. And the filters can be employed just as described above.

The following examples will more clearly illustrate certain aspects of the invention. The following describes various embodiments of dark field inspection tools and methods for their use. In particular, embodiments of the present invention include an illumination source for directing a light beam onto an inspection surface to create scattered light profiles associated with the surface characteristics of the inspection surface. Such surface characteristics include without limitation, variations in surface topography and variations in optical properties (e.g., refractive index) of the materials of the surface. Among the more common surface characteristics giving rise to scattering profiles are so-called phase shift structures coming in to wider usage. A scanning element moves either the beam or the inspection surface so that the beam scans a path across all the desired surfaces of the inspection surface. The resulting scattered light from the surface is received by the photosensitive elements of a photo detector array where it is collected and used to generate images which can be used to characterize the inspection surface.

Figure 5:
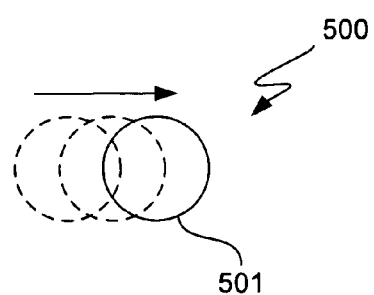
FIG. 5 schematically depicts a laser dot being scanned across an inspection surface in accordance with the principles of the present invention.

In a die-to-die approach FIG. 5 schematically depicts one embodiment of a scanning light dot 501. The depicted light dot 501 is circular, having a spot size of about 3μ in diameter. In one embodiment, the dot 501 is scanned over the surface of the work piece (for example in 1μ increments). As explained previously, other shapes for the light dot 501 can be used. This is depicted in FIG. 5, which depicts each of the incremental movements of the dot 501 (depicted by the dashed dots) as it is scanned across the surface of the work piece. As the dot advances from one position to another, an image is taken of the light scattered from the inspection surface. Each of these images corresponds to a discrete inspection point on the surface of the work piece. As is known to those having ordinary skill in the art, the invention can be practiced using many different scanning patterns to inspect a surface.

FIG. 6(*a*) is a simplified schematic plan view of an example inspection surface 601. As previously explained, a wide variety of surfaces can be inspected in accordance with the principles of the present invention. The depicted surface is a semiconductor wafer 601 having formed thereon a plurality of substantially similar semiconductor die patterns 602 (also referred to in this patent as die or dice). The depicted circle 603 encloses a plurality of semiconductor dice 602. As the light beam is scanned over the wafer 601, an image can be taken for each inspection point (or a subset of inspection points). Images corresponding to the same inspection point on a plurality of dies can then be evaluated to identify bright pixels suitable for adaptively filtering.

As a light beam is scanned over the wafer 601, a stream of images capturing the various scattering patterns is generated. Electronic circuitry can be used to capture, store, filter, or otherwise process this information.

FIGS. 6(*b*) and 6(*c*) are simplified close-up views of a portion 603 of the wafer 601 depicted in FIG. 6(*a*). As a light beam is scanned across the semiconductor wafer 601, a series of inspection points is illuminated. As explained, an image is generated for each inspection point of interest. The images produced for each inspection point on a die can be compared with images produced for an analogous inspection point on every other die on the wafer 601.

FIG. 6(*b*) shows five substantially similar dies (1, 2, 3, 4, and 5) formed on the wafer 601. Each die is scanned as part of a scanning pattern that includes a series of inspection points. A two-dimensional image is generated for each inspection point. These images can be compared to locate defects. Each die is shown with a first inspection point 611 depicted (indicated by the dots). Each inspection point 611 corresponds to the same relative location (x, y) (e.g., for die 1 location $x_1, y_1$, for die 2 location $x_2, y_2$, for die 3 location $x_3, y_3$, and so on) on each other die of the wafer. Of course, the indicated inspection points 611 represent only one of many millions of possible inspection points on each die. The images generated by each first inspection point 611 are compared with images for a corresponding inspection point 611 on each other die (or alternatively, to a database generated reference image) to find patterns of light and dark regions. These images define a set of images for each given point on a die. These image sets can then be used to generate filter templates (also called filters). Methods for achieving such filtering are discussed below.

In continuation, during scanning of the entire wafer, as each die is scanned, additional inspection points are illuminated and images are taken of these scattering patterns. FIG. 6(*c*) shows the same wafer as in FIG. 6(*b*) (e.g., dies 1, 2, 3, 4, and 5) with a different group of inspection points 612 depicted. In the depicted embodiment, each inspection point 612 corresponds to another location (x', y') that is the same for each die (e.g., for die 1 location $x_1', y_1'$, for die 2 location $x_2', y_2'$, for die 3 location $x_3', y_3'$, and so on). Thus, images captured from these inspection points refer to a different location on the die and are subject to another individualized filtering.

Figure 7:
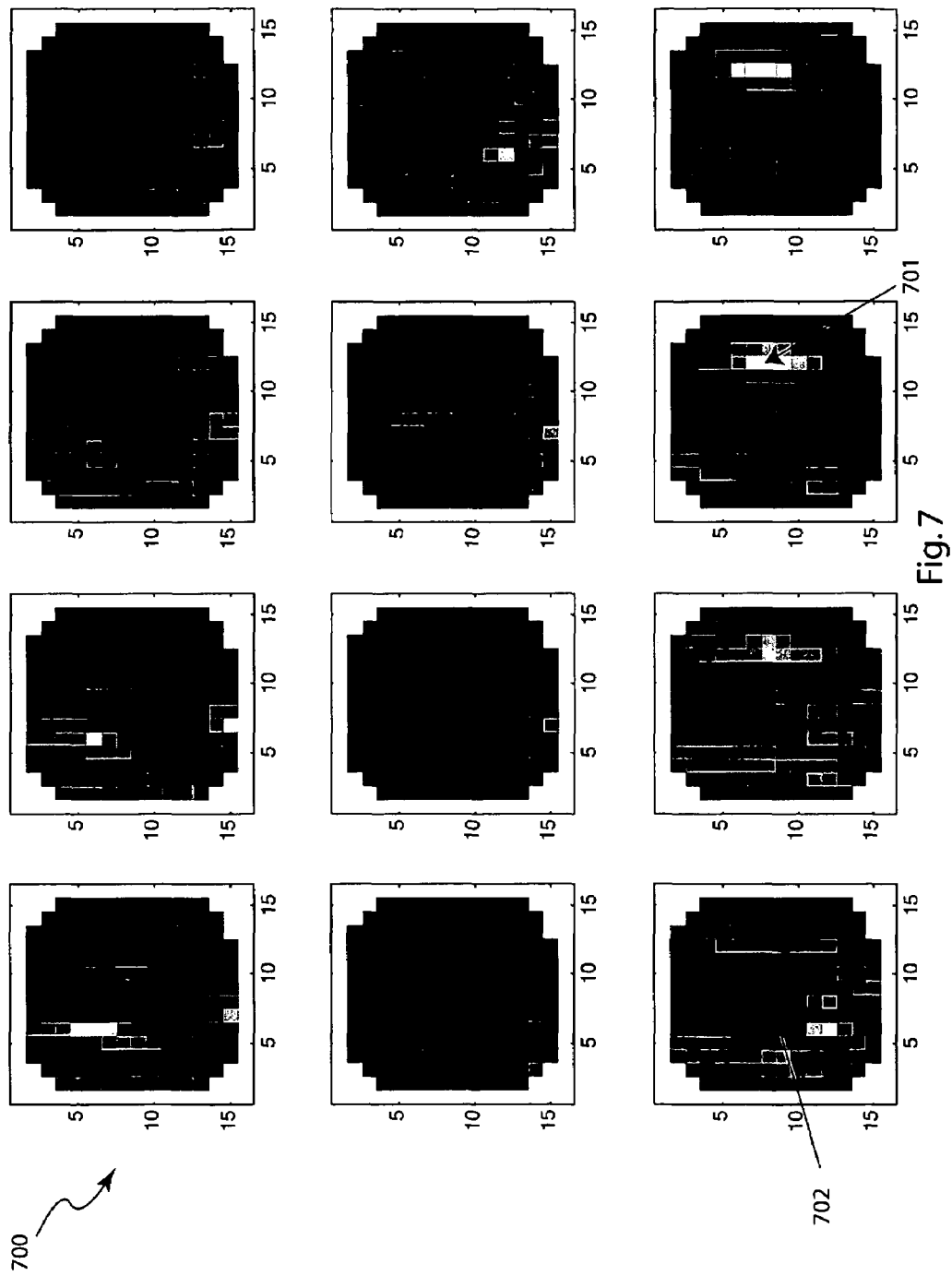
FIG. 7 shows a typical stream of images taken of light scattering patterns produced as a light beam is scanned across an inspection surface in accordance with the principles of the present invention.

FIG. 7 shows one example of a stream of sample images 700 taken of scattering patterns as the light beam is scanned across a wafer. The depicted image stream is detected using a photo detector array having 256 photosensitive elements. This photo detector array is used to capture a stream of images for a die as it is scanned. FIG. 7 shows a series of 12 sample images captured sequentially as a light beam is scanned across the wafer. The depicted sample images 700 each comprise patterns of light regions 701 and dark regions 702. It is noted that these patterns of light and dark regions are analogous to the light intensity pattern depicted in FIG. 4. These patterns of light and dark regions can be used to identify defects in the wafer surface. In the absence of defects, a similar stream of sample images taken from equivalent locations on another die should appear nearly identical to the depicted image stream. Differences in the image streams can be used to identify points on the inspected surface that may have defects.

By comparing the patterns of dark regions taken from the same relative location on a plurality of dies defects can be located. In the absence of defects, each of the images for the same location on a plurality of different dies should look substantially the same. Thus, most images for the same location should have the same pattern of dark regions. Since most images are defect-free, these similar patterns of dark regions can be used as a reference pattern. If there were no defects in any of the inspection points, each of the images for the inspection points will look substantially the same (within some predetermined tolerance). If the pattern of dark regions in some images is lighter than an analogous pattern of dark regions in a reference image, the inspection points associated with those images can be identified as defect candidates. These candidates can be subjected to further analysis with other inspection methods and tools.

Once the images are captured by the photodetector array, they are processed by the electronic circuitry of the device. Such processing can include storage, data manipulation, and a host of other data processing operations known to those having ordinary skill in the art. Importantly, one operation performed by the electronic circuitry is adaptive fourier filtering.

Figure 8:
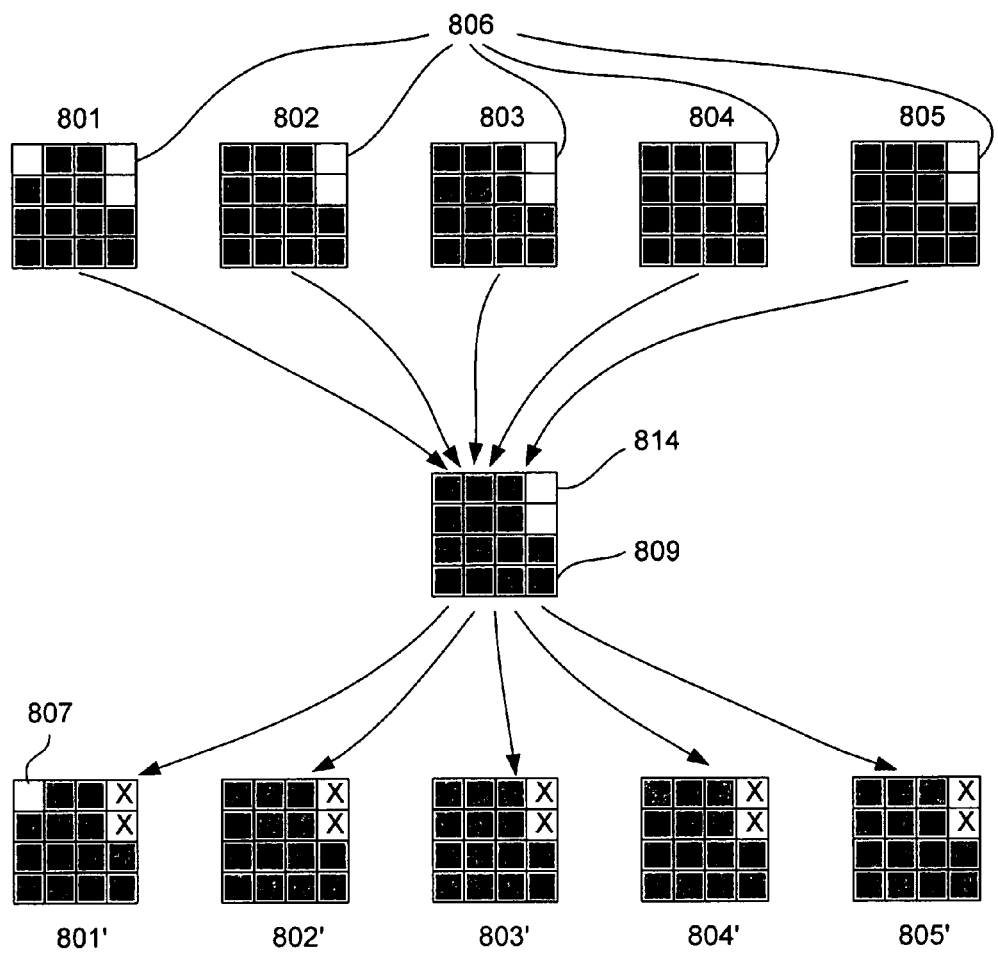
FIG. 8 is a simplified illustration depicting a set of original images used to generate an associated filter which is used to filter the original images which are used to identify defects in accordance with the principles of the present invention.

A simplified example of image comparison process used to define "bright" pixels is depicted in FIG. 8. An inspection point at a first location on a first die is illuminated and forms a scattering pattern. A simplified sixteen-pixel photo detector array produces a first image 801 of the associated scattering pattern. At an analogous (equivalent) inspection point on a second die, a second sample image 802 is captured. Another inspection point at an analogous inspection point on a third die is illuminated and forms a third image 803, and so on until sample images 804 and 805 are also formed. It is noted that all images have a common light region 814 and have largely good agreement in the extent of the dark regions. The sample images 801, 802, 803, 804, and 805 are compared and processed and a reference image 806 depicting the "bright" pixels is shown. For example, the reference image can be a pattern that the majority of the images conform to. Alternatively, a pixel-by-pixel analysis can be conducted wherein each pixel is classified as a "dark" pixel or a "light" pixel and then a comparison can be conducted to find pixels that are lighter than a pixel classified as a "bright" pixel. In this depiction, the reference image 806 is generated that includes a bright region 807 comprising two pixels. This image corresponds to the normal scattering pattern (in the absence of defects) exhibited by the subject inspection point. This image 806 defines the filter template or filter used to filter the associated set of images.

The results of the filtering are shown by filtered images 801', 802', 803', 804', and 805'. The "bright" pixels are removed (indicated by the "X") by the filtering. It can be seen that pixel 807 of the first filtered image 801' is different. Pixel 807 of the first image 803' is significantly lighter than that of the pattern of dark regions of the other filtered images 802', 803', 804', and 805'. This indicates that there is a change in the light scattering pattern from the inspection point associated with the first image 801 (801') and die. This can indicate the presence of a defect at the selected inspection point on the first die. Thus, the selected inspection point on the first die is a defect candidate. Of course, in reality the cases are much more difficult to discern.

In actual embodiments of the invention there are frequently intermediate degrees of light cast on the pixels of the dark patterns. That there are many varying degrees of brightness is well indicated with respect to FIG. 4. Highly specialized algorithms known to those having ordinary skill in the art can be employed to identify those pixels in a set of images that are bright. Methods for identifying and characterizing brightness peaks are known to the skilled practitioner and will not be described in detail here. As has already been noted elsewhere in this patent, the bright pixels are so bright that they decrease the signal-to-noise ratio of the system and hence its sensitivity to defect detection. By filtering out the brightest pixels and evaluating only the remaining dark pixels the S/N ratio can be substantially increased. Moreover, because this process is achieved by data filtering, it can be readily adapted to any surface conformation and is therefore not limited to memory cells or other regularly repeating surface patterns. Additionally, because data filtering is involved any thresholds or other criterion can be altered after the fact to improve the capabilities of the method allowing full evaluation flexibility to a process engineer.

Once filtered, the images can be compared to identify defects. For example, when examining wafers that have not had many process steps performed on them or when used to inspect pattern masks, very low thresholds can be set making the process very sensitive to the presence of bright pixels. Alternatively, when examining wafers that have had many layers formed on their surface (and therefore rather larger pattern variability due to accumulated errors in processing), higher thresholds can be set to reduce the incidence of false positive, but also reduce the sensitivity to the presence of defects. As indicated previously, in some implementations, all the pixels need not be compared. For example, in one implementation the darkest quartile of pixels of the reference image are selected as a subset for comparison. Thus, each comparison image compares an analogous subset of pixels to the selected subset of pixels of the reference image. Such an implementation is effective at improving defect detection in the presence of certain types of noise.

The inventors contemplate that many different methods of filtering the pixels can be employed in accordance with the principles of the invention. A few non-limiting examples are now discussed in the interest of providing suitable illustrations. Once an image is collected a predetermined energy threshold can be set to filter the image. For example, a threshold can be set at 10% of the total energy. Then the image is evaluated for total energy received by all pixels. Then pixels containing the brightest signal (the most energy) are eliminated until a set of pixels remains, with that set of pixels comprising about 10% of the original energy. For example, all of the pixels could be ranked in order of brightness. Then pixels are successively eliminated in order of decreasing brightness until only 10% of the energy remains in the pixels left. The remaining pixels are then evaluated to identify defects. Of course, thi threshold can be adjusted as needed by the user. In one example, the energy threshold could be reduced to 1%. In such cases the rate of false positives could be reduced. The inventors restate that these are just examples and many more methods can be employed in accordance with the principles of the invention.

Figure 9:
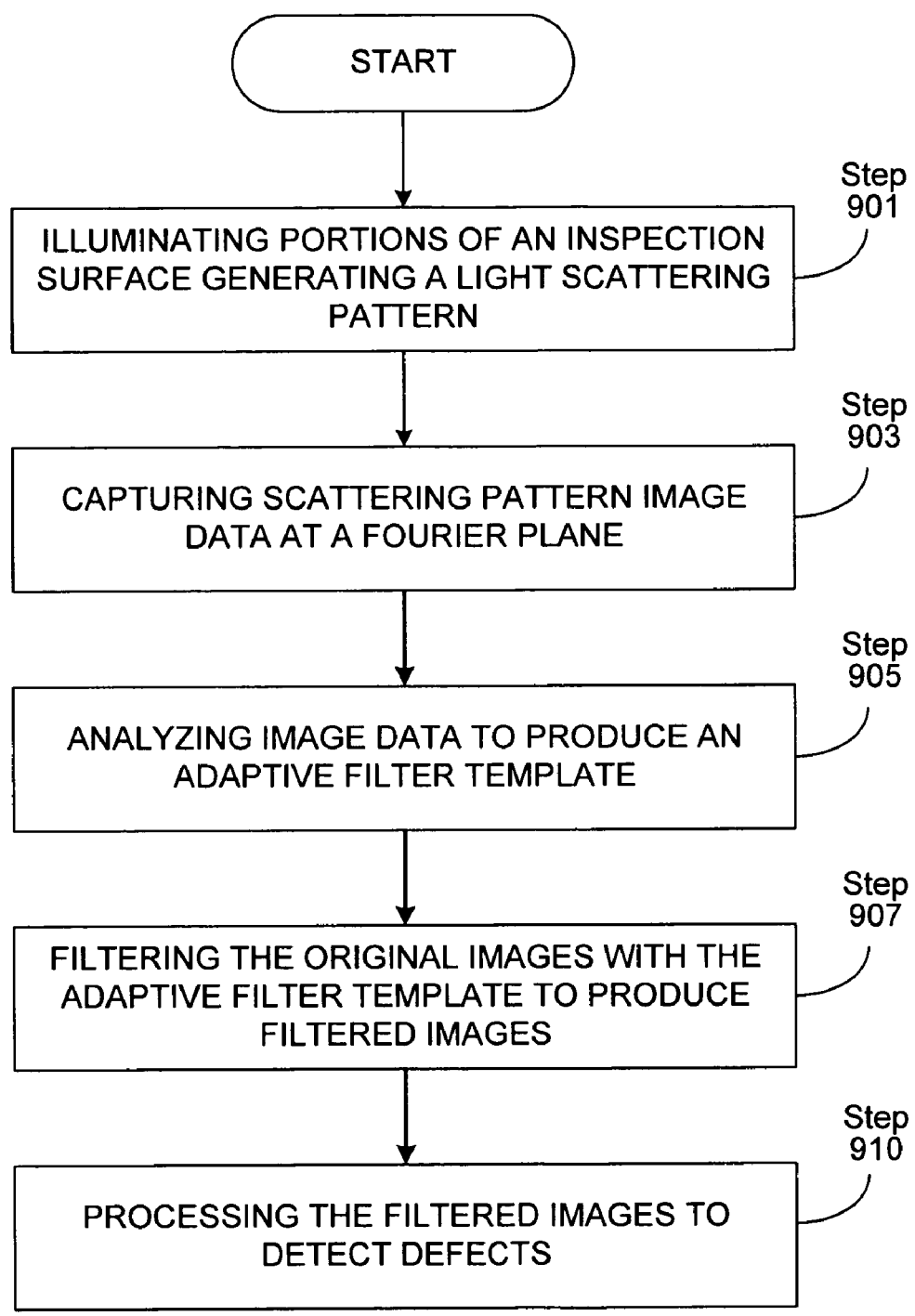
FIG. 9 is a simplified flow diagram illustrating one particular embodiment of a process for adaptive fourier filtering and defect detection in accordance with the principles of the present invention.

FIG. 9 is a flow diagram illustrating an embodiment of a process for inspecting a surface of a work piece in accordance with the principles of the present invention. Such a surface inspection method comprises illuminating selected portions of an inspection surface with a light beam, thereby generating a light scattering pattern associated with the selected portions of the inspection surface (Step 901). In one embodiment, the inspection surface is provided having a die pattern formed thereon. Suitable inspection surfaces include, but are not limited to, semiconductor wafers and mask reticles. Such scanning includes scanning a plurality of inspection points on the inspection surface, thereby generating light scattering patterns associated with the characteristics of the inspection points.

Image data concerning the scattering patterns is then captured at a fourier plane (Step 903). The image data comprises a two-dimensional image associated with the light scattering pattern for each of the selected portions of said surface. The two-dimensional images comprise an array of image pixels containing image information such as the intensity of the scattered light and the two-dimensional position of the scattered light. These captured light scattering patterns are stored as images along with the associated illumination location (inspection point). In this way these images can be compared at the same inspection point in multiple dies.

The image data to is then analyzed to produce an adaptive filter template for each selected portion of said surface (Step 905). The filter enabling the selective removal of particular image pixels from an image associated with the selected portion of said surface. This process can include defining which image pixels are bright and suitable as filter pixels and identifying the position of the bright pixels in the array of image pixels. Using these filter pixels an adaptive filter template for each selected portion of the inspection surface is formed.

In an important alternative embodiment, the Steps of 901-903 are not required. In other words, this implementation does not require the image data obtained by scanning the substrate to generate the filters. Instead, the filters are generated using by analyzing a data model of the target substrate. The model provides a predicted scattering pattern for the surface. The predicted "bright" pixels are identified using standard methods. Accordingly, these pixels are used to generate a filter that can be used in accordance with the principles of the invention.

The original images are then filtered using the appropriate filter template (Step 907). This template is configured to selectively remove the bright pixels from each image to produce a filtered image while still retaining all of the original image data. These filtered images can optionally be further processed in a number of ways.

In one implementation, the filtered image can be analyzed to identify defects in the inspection surface (Step 910). This is accomplished using defect detection algorithms known to those having ordinary skill in the art. The only difference being that the algorithm are operating on the filtered images rather than the raw images captured by the photodetector array.

In short, the photodetector array captures an image of the scattering pattern from each scanned inspection point on a plurality of dies. A normal scattering pattern (unaffected by the presence of defects) for each portion of the inspected surface can be determined. The normally bright areas of the normal scattering pattern can be mapped into a filter template (filter). The individual images associated with the filter are then filtered to produce a set of filtered images. Defects can then by examining and analyzing the filtered images. The process is made more sensitive by examining only the dark (unfiltered) pixels.

The present invention has been particularly shown and described with respect to certain preferred embodiments and specific features thereof. However, it should be noted that the above-described embodiments are intended to describe the principles of the invention, not limit its scope. Therefore, as is readily apparent to those of ordinary skill in the art, various changes and modifications in form and detail may be made without departing from the spirit and scope of the invention as set forth in the appended claims. Other embodiments and variations to the depicted embodiments will be apparent to those skilled in the art and may be made without departing from the spirit and scope of the invention as defined in the following claims. Further, reference in the claims to an element in the singular is not intended to mean "one and only one" unless explicitly stated, but rather, "one or more". Furthermore, the embodiments illustratively disclosed herein can be practiced without any element which is not specifically disclosed herein.

We claim:

1. A dark field surface inspection tool comprising:
    an illumination system configured to scan a light beam across an inspection surface, thereby generating light scattering patterns associated with selected portions of the inspection surface;
    a photodetector array arranged at a fourier plane to receive the light scattering patterns from the work piece, the array comprising a two-dimensional array of light sensitive pixels configured to capture two-dimensional images of the light scattering patterns, wherein selected pixels can be selectively turned on and off in response to filtering instructions received from filtering circuitry; and
    the filtering circuitry for receiving the images at the photodetector array and conducting adaptive fourier filtering of image data to selectively filter image pixels to enhance signal to noise ratio in the remaining image pixels by selectively turning off a pattern of selected pixels of the photodetector array such that only dark portions of photodetector array remain active.

2. A dark field surface inspection tool for inspecting an inspection surface selected from among a plurality of substantially similar inspection surfaces, the tool comprising:
    an illumination system configured to scan a light beam across an inspection surface, thereby generating light scattering patterns associated with selected portions of the inspection surface wherein the light beam illuminates the same selected portion of each of the plurality semiconductor dies to generate light scattering pattern associated with the selected portion of the inspection surface;
    a photodetector array arranged at a fourier plane to receive the light scattering patterns from the work piece, the array comprising a two-dimensional array of light sensitive pixels configured to capture two-dimensional images of the light scattering patterns wherein the photodetector array captures two-dimensional images of the light scattering patterns of the same selected portion of the plurality semiconductor dies with each image corresponding to an equivalent portion on a different die;
    circuitry for receiving the images and conducting adaptive fourier filtering of image data to selectively filter image pixels to enhance signal to noise ratio in the remaining image pixels wherein the circuitry includes,
        circuitry configured to process the images to generate a filter template capable of selectively filtering the image pixels of each image to enhance signal to noise ratio of each filtered image;
        circuitry configured to process each image with an associated template to obtain the filtered image for the associated selected portion of the inspection surface; and
        circuitry configured to process the filtered image to detect defects for the associated selected portion of the inspection surface.

3. The dark field surface inspection tool of claim 2 wherein the photodetector array a two-dimensional array of light sensitive pixels comprising 256 photosensitive elements.

4. The dark field surface inspection tool of claim 3 wherein the photosensitive elements of the photodetector array are positioned such that the array subtends a solid angle of greater than about 40°×40°.

5. The dark field surface inspection tool of claim 2 wherein the light scattering pattern generated by the light beam forms a pattern of bright regions and dark regions associated with the selected portion of a die;
    wherein the photodetector array captures two-dimensional images of the pattern of bright regions and dark regions associated with the selected portion of the die;
    wherein the circuitry configured to process the images to generate a filter template are configured to define a set of bright pixels for each selected portion of the inspection surface and generate a filter template associated with the set of bright pixels; and
    wherein the circuitry configured to process the image with an associated template to obtain the filtered image is configured to selectively remove the pixels associated with the set of bright pixels from the image to generate the filtered image.

6. The dark field surface inspection tool of claim 2 wherein the circuitry enables the identification of defects at the selected portions of the inspection surface.

7. A method of adaptively filtering of image data, the method comprising:
    illuminating selected portions of an inspection surface with a light beam, wherein the inspection surface comprises a surface having a plurality of substantially similar semiconductor die patterns formed thereon, said illuminating thereby generating a light scattering pattern associated with the selected portions of the inspection surface;
    capturing image data at a fourier plane wherein the image data is associated with the light scattering pattern for each of the selected portions of said surface, wherein the image data comprises a two-dimensional image comprised of an array of image pixels; and
    adaptively filtering the image data to produce an adaptively filtered image wherein said adaptively filtering the image pixels includes,
    conducting a die to die comparison of a same portion of each die pattern to identify a set of pixels suitable for adaptive filtering; and generating a unique adaptive filter template for each inspected portion of the die pattern wherein the filter template enables the selected image pixels to be filtered out from image data.

8. The method of claim 7, wherein the die to die comparison comprises:
obtaining a set of images for the portion of each die pattern;
comparing the pixels of each set of images to identify a pattern of bright and dark pixels wherein the bright pixels are identified as the set of pixels suitable for filtering; and
wherein generating the unique adaptive filter template for each portion of the die pattern comprises generating a filter configured to filter out data from said bright pixels.

9. The method of claim 8, wherein the bright pixels are defined as pixels in a set of images associated with a portion of a die having a brightness above a predetermined brightness level.

10. The method of claim 8, wherein the bright pixels are defined as the brightest percentage of pixels in an image associated with a portion of a die wherein the percentage comprises a predetermined brightness threshold percentage.

11. The method of claim 8, wherein the bright pixels are defined as the brightest percentage of pixels in an image associated with a portion of a die wherein the percentage comprises a predetermined brightness threshold percentage.

12. The method of claim 8, wherein the bright pixels are defined as a group of pixels having a cumulative energy level above a predetermined energy threshold percentage.

13. The method of claim 7, wherein illuminating selected portions of an inspection surface comprises illuminating a die pattern wherein the selected portions comprise random logic features.

14. The method of claim 7, wherein adaptively filtering the image pixels includes,
analyzing a data model associated with the inspection surface to identify, for each inspected portion of the surface, a set of pixels suitable for adaptive filtering; and
incorporating each set of pixels into a unique adaptive filter template, wherein each filter template is suitable for filtering data associated with its associated inspected portion of the surface.

15. The method of claim 7, wherein the inspection surface comprises a surface having a plurality of substantially similar semiconductor die patterns formed thereon; and
adaptively filtering the image pixels includes,
using a data model of the die pattern to identify a set of pixels suitable for adaptive filtering; and
generating a unique adaptive filter template for each inspected portion of the die pattern wherein the filter template enables the selected image pixels to be filtered out from image data.

16. The method of claim 15, wherein using the data model of the die pattern to identify a set of pixels suitable for adaptive filtering includes analyzing the light scattering pattern predicted by the model to identify a pattern of bright and dark pixels wherein the bright pixels are identified as the set of pixels suitable for filtering; and
wherein generating the unique adaptive filter template comprises generating a filter configured to filter out data from said bright pixels.

17. The method of claim 16, wherein the bright pixels are defined as pixels in a set of images associated with a portion of a die having a brightness above a predetermined brightness level.

18. The method of claim 16, wherein the bright pixels are defined as a group of pixels having a cumulative energy level above a predetermined energy threshold percentage.

19. The method of claim 7, wherein adaptively filtering the image data includes,
generating an image pattern of bright and dark pixels associated with each inspection point on the inspection surface;
selecting a set of bright pixels for each image pattern to identify a set of filtering pixels suitable for adaptive filtering; and
using the set of filtering pixels to generate a unique adaptive filter template for each image pattern, the filtering pixels enabling selected image data to be filtered out from image data.

20. The method of claim 19, wherein the bright pixels are defined as pixels having a brightness above a predetermined brightness level.

21. The method of claim 19, wherein the bright pixels are defined as the brightest percentage of pixels in each image associated with a particular inspection point.

22. A method of adaptively filtering of image data, the method comprising:
illuminating selected portions of an inspection surface with a light beam, thereby generating a light scattering pattern associated with the selected portions of the inspection surface;
capturing image data at a fourier plane wherein the image data is associated with the light scattering pattern for each of the selected portions of said surface, wherein the image data comprises a two-dimensional image comprised of an array of image pixels;
analyzing the image data to produce an adaptive filter template for each selected portion of said surface enabling the selective removal of particular image pixels from an image associated with the selected portion of said surface;
applying the template to the image data captured at the fourier plane thereby selectively excluding said particular image pixels to obtain a filtered image; and
analyzing the filtered image to identify defects in the inspection surface.

23. The method of claim 22 wherein
the two-dimensional array of image pixels captured at a fourier plane comprises a pattern of bright and dark pixels;
wherein analyzing the image data to produce an adaptive filter template for each selected portion of said surface comprises,
defining which of the image pixels are bright and identifying the position of the bright pixels in the array of image pixels,
defining an adaptive filter template for each selected portion of the inspection surface, the template configured to selectively remove the bright pixels from the image while still enabling data associated with the dark pixels to be evaluated; and
wherein applying the template to the image data captured at the fourier plane comprises selectively excluding the bright pixels to obtain a filtered image.

24. The method of claim 23 wherein the method is embodied as a computer program product embodied on a computer readable media including computer program code for accomplishing adaptively filtering of image data, program product including:
computer readable instructions for said illuminating the selected portions, computer readable instructions for said capturing the two-dimensional array of image pixels captured at the fourier plane as a pattern of bright and dark pixels;

computer readable instructions for said analyzing the image data to produce the adaptive filter template for each selected portion of said surface enabling the selective removal of particular image pixels from an image associated with the selected portion of said surface;

computer readable instructions for said applying the template to the image data captured at the fourier plane thereby selectively excluding said particular image pixels to obtain a filtered image; and computer readable instructions for said analyzing the filtered image to identify defects in the inspection surface.

25. The method of claim 23 wherein the method is embodied as a computer program product embodied on a computer readable media including computer program code for accomplishing adaptively filtering of image data, program product including:

computer readable instructions for said illuminating the selected portions, computer readable instructions for said capturing the two-dimensional array of image pixels captured at the fourier plane as a pattern of bright and dark pixels;

computer readable instructions for said analyzing the image data to produce the adaptive filter template for each selected portion of said surface comprises:

computer readable instructions enabling said defining which of the image pixels are bright and identifying the position of the bright pixels in the away of image pixels, computer readable instructions for said defining of the adaptive filter template for each selected portion of the inspection surface enabling selective removal of the bright pixels from the image while still enabling data associated with the dark pixels to be evaluated;

computer readable instructions for said applying the template to the image data captured at the fourier plane thereby selectively excluding said bright pixels to obtain a filtered image; and computer readable instructions for said analyzing the filtered image to identify defects in the inspection surface.

26. The method of claim 22, wherein the inspection surface comprises a surface having a plurality of substantially similar semiconductor die patterns formed thereon; and wherein analyzing the image data to produce an adaptive filter template for each selected portion of said surface enabling the selective removal of particular image pixels from an image associated with the selected portion of said surface comprises, conducting a die to die comparison of a same portion of each die pattern to identify a set of pixels suitable for adaptive filtering; and generating a unique adaptive filter template for each inspected portion of the die pattern wherein the filter template enables the selected image pixels to be filtered out from image data.

27. The method of claim 26, wherein the inspection surface comprises a surface having a plurality of substantially similar semiconductor die patterns formed thereon and wherein the method is embodied as a computer program product embodied on a computer readable media including computer program code for accomplishing adaptively filtering of image data, program product including:

computer readable instructions for said illuminating the selected portions, computer readable instructions for said capturing the two-dimensional array of image pixels captured at the fourier plane as a pattern of bright and dark pixels;

computer readable instructions for said analyzing the image data to produce the adaptive filter template for each selected portion of said surface comprises:

computer readable instructions enabled said conducting a die to die comparison of a same portion of each die pattern to identify a set of pixels suitable for adaptive filtering; and computer readable instructions for enabling said generation of a unique adaptive filter template for each inspected portion of the die pattern wherein the filter template enables the selected image pixels to be filtered out from image data.

28. A method of inspecting a substrate, the method comprising:

applying a fourier filter model to a pattern on an inspection surface to generate a modeled fourier image for every point on the pattern to generate a library of stored modeled fourier images associated with the pattern wherein each modeled image comprising a modeled fourier pattern of light and dark regions;

illuminating desired portions of the pattern of the inspection surface with a light beam, thereby generating a light scattering pattern associated with the selected portions of the inspection surface;

capturing image data for each desired portion of the pattern with an image sensor at a fourier plane;

processing the captured image data together with associated modeled fourier images such that only captured image data that corresponds to the dark regions of the associated modeled fourier images are used to generate an associated enhanced signal to noise ratio image; and analyzing the enhanced image to identify defects in the inspection surface.

29. The method of claim 28, wherein illuminating selected portions of an inspection surface comprises illuminating a die pattern wherein the selected portions comprise random logic features.

30. A method of inspecting a substrate, the method comprising:

providing an inspection surface having a plurality of substantially identical patterns formed thereon;

conducting illumination of various portions of each pattern on the surface;

capturing initial fourier patterns of images formed by each illuminated portion of each pattern;

processing the initial images such that images taken from the same portion of each of the patterns are processed together to define an aggregate pattern image of light and dark regions for each portion of the pattern defining a filter library for the pattern;

processing an initial fourier image from a portion of the pattern together with an aggregate pattern image associated with the same portion of the pattern such that only initial fourier image data that corresponds to the dark regions of the associated aggregate pattern image are used to generate an associated enhanced signal to noise ratio image; and analyzing the enhanced image to identify defects in the inspection surface.

* * * * *